United States Patent
Parr et al.

[11] Patent Number: 4,744,793
[45] Date of Patent: May 17, 1988

[54] PROSTHETIC LIGAMENT CONNECTION ASSEMBLY

[75] Inventors: Jack E. Parr, North Webster; Robert L. Fuson, Warsaw, both of Ind.

[73] Assignee: Zimmer, Inc., Warsaw, Ind.

[21] Appl. No.: 773,286

[22] Filed: Sep. 6, 1985

[51] Int. Cl.⁴ .............................................. A61F 2/58
[52] U.S. Cl. .......................................... 623/13; 623/16
[58] Field of Search ..................... 128/334 C, 334 R; 623/1, 13, 16–23, 1

[56] References Cited

U.S. PATENT DOCUMENTS

| | | | |
|---|---|---|---|
| 2,453,056 | 11/1948 | Zack | 128/334 C |
| 3,953,896 | 5/1976 | Treace | 3/1 |
| 3,973,277 | 8/1976 | Semple | 3/1 |
| 4,149,277 | 4/1979 | Bokros | 3/1 |
| 4,187,558 | 2/1980 | Dahlen | 3/1 |
| 4,301,551 | 11/1981 | Dore et al. | 3/1 |
| 4,366,819 | 1/1983 | Kaster | 128/334 C |
| 4,400,833 | 8/1983 | Kurland | 3/1 |
| 4,447,915 | 5/1984 | Weber | 623/16 |
| 4,509,516 | 4/1985 | Richmond | 128/303 |
| 4,523,587 | 6/1985 | Frey | 128/92 |
| 4,605,414 | 8/1986 | Czajka | 623/13 |

OTHER PUBLICATIONS

Leeds–Keio Ad British Jbjs. No. 4, Aug. 1985.
Leeds–Keio Ad British Jbjs No. 7, Mar. 1984.
Murray et al., "Transfer of Tensile . . . " Jbjs vol. 63 B No. 1, 1981.
Clancy et al. "Treatment of . . . " Jbjs vol. 65-A, No. 3, Mar. 1983.

Primary Examiner—V. Millin
Assistant Examiner—David J. Isabella
Attorney, Agent, or Firm—Paul D. Schoenle

[57] ABSTRACT

A prosthetic ligament connection assembly includes a plug adapted to fit within an opening in a bone so that the prosthetic ligament in the opening will be secured to the bone via a uniform interface therebetween.

5 Claims, 1 Drawing Sheet

PROSTHETIC LIGAMENT CONNECTION ASSEMBLY

The present invention relates to the connection of a prosthetic ligament to a bone or the like.

Heretofore, prosthetic ligaments have been used in surgery to repair and/or replace natural ligaments which have been damaged. In order to attach the prosthetic ligament to the bone, a staple or bone screw is inserted over or through the prosthetic ligament and coupled to bone. Obviously, such procedure cuts a portion of the prosthetic ligament which could fail in tension or tear as the ligament is constantly under tension during normal physical activity. In the case of a staple the prosthetic ligament can slip under tension if the staple is not tight or loosens. To overcome the problem with staples and screws, it has been proposed to provide a plug connected to an end of the prosthetic ligament and adapted for disposition in an opening formed in a bone. With this situation there is no adjustment at the end of the prosthetic ligament so that surgical techniques are limited in establishing the proper tension for the prosthetic ligament. In addition, a plug of bone has been used to trap the prosthetic ligament in a bone opening, however, this procedure pinches portions of the prosthetic ligament so that tears in the prosthetic ligament are more than likely.

The present invention provides a connection assembly between a prosthetic ligament and a bone that generates a substantially uniform locking force on the prosthetic ligament and also is easily adjustable during surgery so that the proper tension can be imparted to the prosthetic ligament. In one form of the invention, a frusto conical opening is provided in bone to be connected with the prosthetic ligament. An anchor plug having a matching frusto conical outer surface is disposed in the opening so that the prosthetic ligament extends through a frusto conical aperture in the anchor plug. The prosthetic ligament is tubular at its end so that a locking plug is inserted in the tubular end to bias the latter into engagement with the wall of the frusto conical aperture on the anchor plug. When the locking plug is advanced into the anchor plug to tightly grip the prosthetic ligament therebetween a uniform gripping force is generated across all of that portion of the prosthetic ligament in engagement with both plugs.

It is an object of a present invention to provide a connection assembly for the prosthetic ligament so that the connection assembly is easily adjusted to lock the prosthetic ligament to the bone and is adapted to generate a uniform locking force against the prosthetic ligament.

Figure 1:
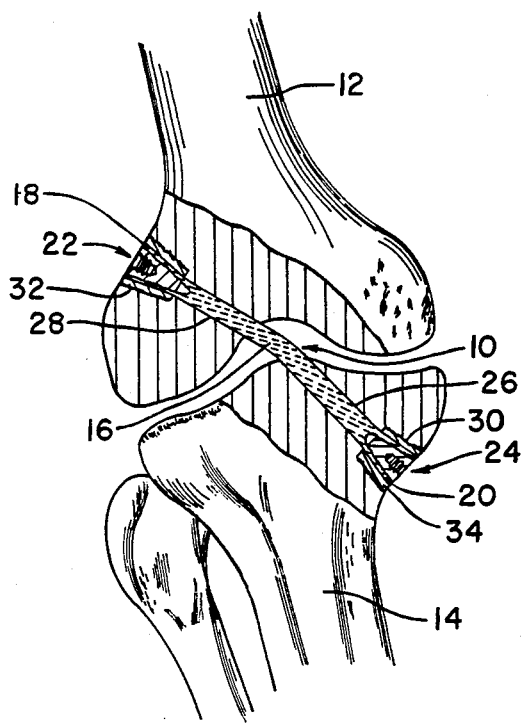
FIG. 1 is a diagrammatic front view of the prosthetic ligament and connection assembly as applied to a femur and a tibia.

A prosthetic ligament 10 is intended to replace an anterior cruciate ligament extending between the distal end of a femur 12 and the proximal end of a tibia 14. The prosthetic ligament 10 includes a center portion 16 extending between the femur 12 and the tibia 14 and a pair of tubular ends or flat ends that may be rolled to form a tube 18 and 20. The end 18 is illustrated in a fully locked position with a connection assembly 22 while a connection assembly 24 cooperates with the end 20. The connection assemblies 22 and 24 are identical so that the following description will proceed with reference only to one connection assembly.

Figure 3:
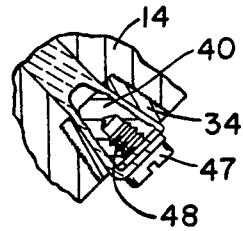
FIG. 3 is a view of the locking plug of FIG. 1 showing a further attachment for the prosthetic ligament to the locking plug.

In order to implant the prosthetic ligament 10, the femur 12 and the tibia 14 are provided with substantially aligned openings 26 and 28. Each opening forms a frusto conical wall 30 and 32 remote from the center portion 16. An anchor plug 34 with a matching frusto conical outer surface 36 is disposed in the opening 26 so that a porous surface on the outer surface 36 is in intimate contact with the bone at wall 30 to enable bony ingrowth for fixation. The anchor plug 34 defines a frusto conical aperture 38 tapering outwardly so that the tubular end 20 of the prosthetic ligament 10 extends through the aperture 38. A locking plug 40 forms a roughened outer frusto conical surface 42 substantially matching the contour for the aperture 38. The locking plug 40 is inserted into the tubular end 20 of the prosthetic ligament with a tool 44 adapted via threads 46 to carry the plug 40 and facilitate insertion thereof into the tubular end 20 and into tight engagement with the prosthetic ligament 10 when the latter is pressed against the anchor plug 34 by the locking plug. With the locking plug 40 fully inserted into the anchor plug 34, the prosthetic ligament is trapped between the plugs and a screw 47, see FIG. 3, may be inserted into a threaded aperture 48 to positively connect the prosthetic ligament to the locking plug 40.

During surgery, the tubular end 20 is pulled outwardly from the aperture 38 until the proper tension is imparted to the prosthetic ligament 10. Then the locking plug 40 is inserted to fixedly connect the prosthetic ligament to the plugs 34 and 40. The tension on the prosthetic ligament 10 generates a restoring force biasing the plugs 34 and 40 inwardly so that any movement, be it slight, further enhances the gripping force of the plugs on the prosthetic ligament as well as the locking fit of the anchor plug 34 to the wall 30 of bone aperture 26. Furthermore, with the surface 42 of locking plug 40 substantially matching the surface for aperture 38, the gripping force applied to the prosthetic ligament is substantially uniform over that portion of the prosthetic ligament engaging both plugs 34 and 40.

Figure 4:
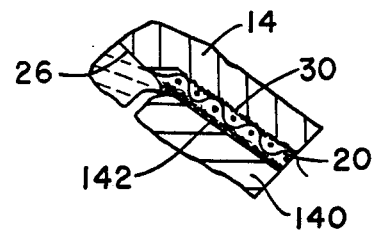
FIG. 4 is a view illustrating another embodiment of the invention herein.
Figure 2:
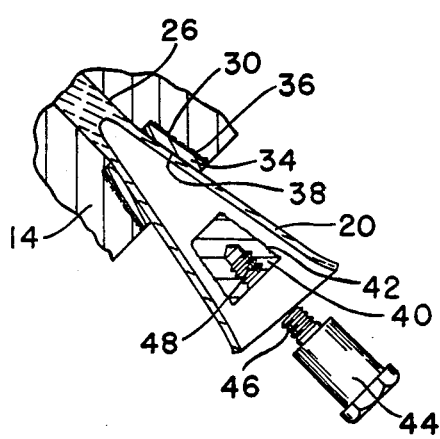
FIG. 2 is an enlarged and exploded view of the connection assembly of FIG. 1.

Turning to FIG. 4, a locking plug 140 is illustrated in the fully installed position. The locking plug 140 includes a porous surface 142 which is engageable with the prosthetic ligament tubular end 20 to bias the latter into engagement with the frusto conical wall 30 of the bone. With the prosthetic ligament 20 forming a first porous surface and the porous surface 142 comprising a second porous surface, it is possible for the bone to grow through the prosthetic ligament and into the porous surface 142, thereby fixedly securing the prosthetic ligament between the plug 140 and the bone.

Figure 5:
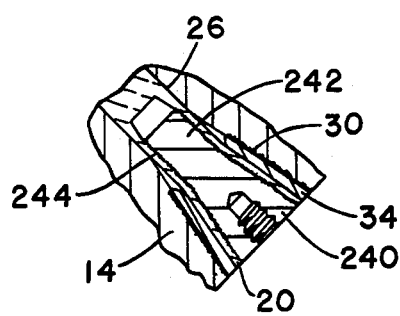
FIG. 5 is a view similar to FIG. 3 illustrating a further embodiment of the invention herein.

Turning to FIG. 5, the locking plug 240 is similar to the locking plug 40 except for an extension 242 extending past the anchor plug 34. The extension 242 is dimensioned to fit in the opening 26 with sufficient clearance therewith to form a tight fit for that portion of the prosthetic ligament trapped between the wall of opening 26 and the extension 242. Furthermore, the extension 242 is provided with a porous outer surface 244 so that bone is free to grow through the porous prosthetic ligament and into the porous outer surface 244.

Although not shown, it is possible for the locking plug to comprise a split ring or an elastomeric element which is radially contracted when inserted in the anchor plug to generate a restoring force further biasing the locking plug into engagement with the prosthetic ligament. Also, the anchor plug may comprise a split ring which is radially expandible into engagement with the wall of bone opening 30.

We claim:

1. A prosthetic connection assembly for attachment of a prosthetic ligament to a bone, the bone defining an opening for receiving the prosthetic ligament wherein said opening defines a frusto conical wall; and said connection assembling comprising a prosthetic ligament having a central portion and at least one substantially hollow tubular end portion;

first and second members, said first member defining a frusto conical outer surface engagable with said opening and a frusto conical inner surface forming an aperture to receive said second member such that the hollow tubular end portion of said prosthetic ligament is positioned between said first and second member establishing a uniform interface between said members and said ligament thereby interlocking and securing said ligament therebetween.

2. The prosthetic ligament connection assembly of claim 1 in which the first member is radially expandable for movement into tight engagement with the bone in response to movement of the second member.

3. The prosthetic ligament connection assembly of claim 1 in which the second member includes a roughened surface engageable with the prosthetic ligament to tightly grip the latter between the members.

4. The prosthetic ligament connection assembly of claim 1 in which the second member is compressed in the interlock position to generate a restoring force biasing the prosthetic ligament into engagement with the first member.

5. The prosthetic ligament connection assembly of claim 1 in which the prosthetic ligament generates a restoring force when attached to the bone and the restoring force is substantially imparted to the second member to further tighten the engagement of the prosthetic ligament between the members.

* * * * *